(12) United States Patent
Hair

(10) Patent No.: US 6,647,282 B2
(45) Date of Patent: Nov. 11, 2003

(54) LASER ADJUSTMENT MECHANISM

(75) Inventor: Steven E. Hair, Woodbury, MN (US)

(73) Assignee: GE Medical Systems Global Technology, Waukesha, WI (US)

( * ) Notice: Subject to any disclaimer, the term of this patent is extended or adjusted under 35 U.S.C. 154(b) by 91 days.

(21) Appl. No.: 09/749,211

(22) Filed: Dec. 27, 2000

(65) Prior Publication Data

US 2002/0115928 A1 Aug. 22, 2002

(51) Int. Cl.[7] .............................. A61B 5/05; A61B 6/08; H05G 1/02
(52) U.S. Cl. ...................... 600/410; 600/425; 378/195; 378/196; 378/206; 372/20
(58) Field of Search .................. 600/407, 410, 600/425; 269/101, 182; 378/206, 195, 196; 372/107, 20

(56) References Cited

U.S. PATENT DOCUMENTS

| | | | | | |
|---|---|---|---|---|---|
| 2,167,114 | A | * | 7/1939 | Kieffer ........................ 378/181 |
| 2,508,449 | A | * | 5/1950 | Davis, Jr. et al. ........ 248/279.1 |
| 4,538,289 | A | * | 8/1985 | Scheibengraber ............ 378/20 |
| 5,247,935 | A | * | 9/1993 | Cline et al. .................. 600/411 |
| 5,570,409 | A | * | 10/1996 | Yamaguchi et al. ........ 378/196 |
| 5,577,095 | A | * | 11/1996 | Kobayashi ................... 378/205 |
| 5,661,667 | A | * | 8/1997 | Rueb et al. .................... 702/95 |
| 5,792,215 | A | * | 8/1998 | Martin et al. ................. 607/88 |
| 5,814,042 | A | * | 9/1998 | Zair ............................ 606/17 |
| 5,933,274 | A | * | 8/1999 | DeSimone .................. 359/390 |
| 5,995,265 | A | * | 11/1999 | Black et al. ................. 359/201 |
| 6,031,888 | A | * | 2/2000 | Ivan et al. ................... 378/196 |
| 6,195,407 | B1 | * | 2/2001 | Dobbs et al. ................. 378/19 |
| 6,267,769 | B1 | * | 7/2001 | Truwit ............................ 606/1 |
| 6,292,221 | B1 | * | 9/2001 | Lichtman .................... 348/345 |
| 6,294,915 | B1 | * | 9/2001 | Murphy et al. ............. 324/318 |

* cited by examiner

Primary Examiner—Henry Bennett
Assistant Examiner—Kathryn Ferko
(74) Attorney, Agent, or Firm—Quarles & Brady LLP; Carl Horton

(57) ABSTRACT

An apparatus is provided for aligning a laser beam with a hidden target. In particular, a coupling is rotated which rotates a laser diode and simultaneously translates the diode to produce a spiral shaped laser beam path. The coupling is continuously rotated until it is determined that the beam has become aligned with the target.

9 Claims, 3 Drawing Sheets

LASER ADJUSTMENT MECHANISM

BACKGROUND OF THE INVENTION

The present invention relates generally to magnetic resonance imaging and, in particular, relates to a method for positioning a laser beam onto a predetermined location to identify a tissue to be imaged.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_t$. A signal is emitted by the excited spins after the excitation signal $B_1$ is terminated. This signal may be received and processed to form an image.

When utilizing these signals to produce images, magnetic field gradients ($G_x$ $G_y$ and $G_z$) are employed. Typically, the region to be imaged is scanned by a sequence of measurement cycles in which these gradients vary according to the particular localization method being used. The resulting set of received NMR signals are digitized and processed to reconstruct the image using one of many well-known reconstruction techniques.

In modern MRI systems, a laser beam is used to define the center location, or sweet spot, of an image of human tissue to be imaged. However, due to mechanical interference with the MRI system, the laser emitting diode is typically mounted onto an outer surface of the MRI system. In order to direct the laser beam radially inwardly towards the patient, the beam is deflected off a mirror that is also mounted on the outer surface of the RF coils. An opening extends radially through the outer surface and provides a conduit for the laser beam to deflect off the mirror radially inwardly to identify the portion of the tissue that will correspond to the sweet spot of the image. Accordingly, once the laser has been calibrated, a patient may subsequently be placed in the MRI system and positioned so that the tissue to be imaged is identified by the laser beam. This will ensure that the sweet spot of the image will correspond to the desired tissue.

However, because the diode is positioned at an appreciable distance from the mirror, and because of the relatively small size of the mirror, and due to tolerances associated with manufacturing, it is highly unlikely that the beam will be in initial alignment with the mirror. For example, if the diode is mis-aligned by as little as ¼°, the beam will not hit the mirror. Furthermore, the laser will be periodically re-calibrated due to vibrations associated with operation of the MRI system.

Moreover, the laser must be adjusted to hit the precise point on the mirror that will yield the desired deflection. Accordingly, the position of the diode will need to be adjusted in the x and y directions so that the beam will deflect off the mirror. One method that could be used to properly align the laser with the mirror is to manually translate the diode in the x and y directions. The user will then rely on sight to determine when the beam becomes deflected off the mirror, which will become apparent when the beam extends through the MRI system in a predictable manner, and onto a predetermined calibration location. In particular, an adjustment lever extends from the laser assembly and out of the MRI system housing that may be manipulated to adjust the position of the diode. However, because the laser beam will be hidden when not properly aligned with the mirror, the user will be unaware what positional adjustments to the diode are necessary. Therefore, the user will essentially be blindly moving the diode at random until the beam hits the mirror. This is an unacceptably tedious, cumbersome, and time-consuming process. Furthermore, the sensitivity of the laser assembly hinders the fine adjustment of the laser beam using this method.

What is therefore needed is an improved method and apparatus for reliably and systematically manipulating a laser diode to align the output laser beam with a desired target location.

SUMMARY OF THE INVENTION

An apparatus for systematically aiming a laser beam to a target is presented having an outer housing extending generally along a central axis, a laser diode operable to emit the laser beam in the general direction of the target, and an adjustable coupling for mounting the laser diode to the outer housing and being operable to systematically move the laser beam in a search path that intersects with the target.

BRIEF DESCRIPTION OF THE DRAWINGS

Reference is hereby made to the following figures in which like reference numerals correspond to like elements throughout, and in which.

DETAILED DESCRIPTION OF THE PREFERRED EMBODIMENT

Figure 1:
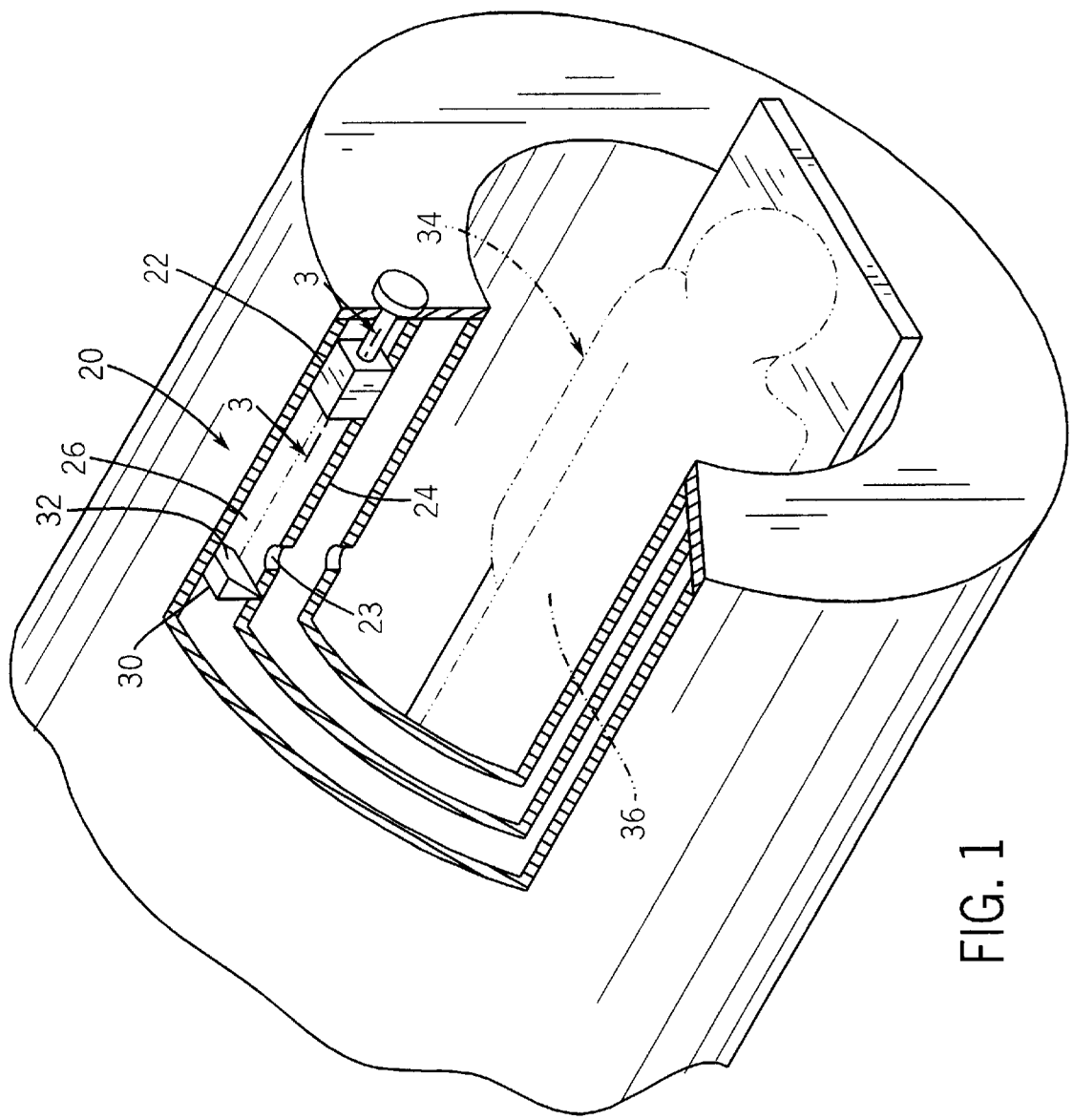
FIG. 1 is a perspective view of a MRI system having a portion cut away to illustrate a laser system constructed in accordance with the preferred embodiment.

Referring initially to FIG. 1, a laser system 20 includes a laser assembly 22 and mirror 30 that are mounted onto a surface 24 of a magnetic resonance device. In particular, the laser assembly 22 and mirror may be mounted onto an outer housing of a RF coil, and surrounded by an outer housing of the MRI system. The laser assembly 22 emits a laser beam 26 from a laser diode 28 (see FIG. 2) onto a mirror 30 having a deflection surface 32, which deflects the beam radially inwardly, and through an aperture 23 extending through surface 24, to identify what will be the sweet spot 36 of an acquired MR image. A calibration device having a calibration surface (not shown) may be inserted into the bore of the MRI system, and the laser adjusted such that the beam impinges on the surface to identify a predefined calibration point.

A patient 34 may then be placed in the MRI system and positioned such that the tissue to be imaged is identified by the laser beam 26. It should be appreciated that the deflection surface 32 is relatively small, and the distance between the laser diode 28 and mirror 30 is great enough such that the laser assembly 22 must be precisely aligned to ensure that the beam will hit the mirror. Moreover, the laser beam 26 must hit the precise point on the deflection surface 32 that will yield the desired deflection.

In one embodiment, a magnetic resonance imaging system that is commercially available from General Electric Company under the trademark Open Speed™ (registration pending), the laser assembly 22 and mirror 30 are mounted onto the outer housing of the RF coil and spaced approximately 585.7 millimeters apart. The MRI system is configured to accept a mirror whose deflection surface 32 has a width of no more than approximately 5 mm. Additionally, because the deflection surface is angled approximately 45° with respect to the laser beam 26, the deflection surface 32 presents an even smaller target for the laser beam 26. For example, it has been found that if the laser diode 28 is misaligned by as little as 1°, the beam 26 will be translated by approximately 10 mm, or twice the width of the deflection surface 32. Accordingly, the sensitivity is such that the laser diode 28 may be misaligned by no more than ¼° in order for the laser beam 26 to hit the deflection surface 32.

Figure 2:
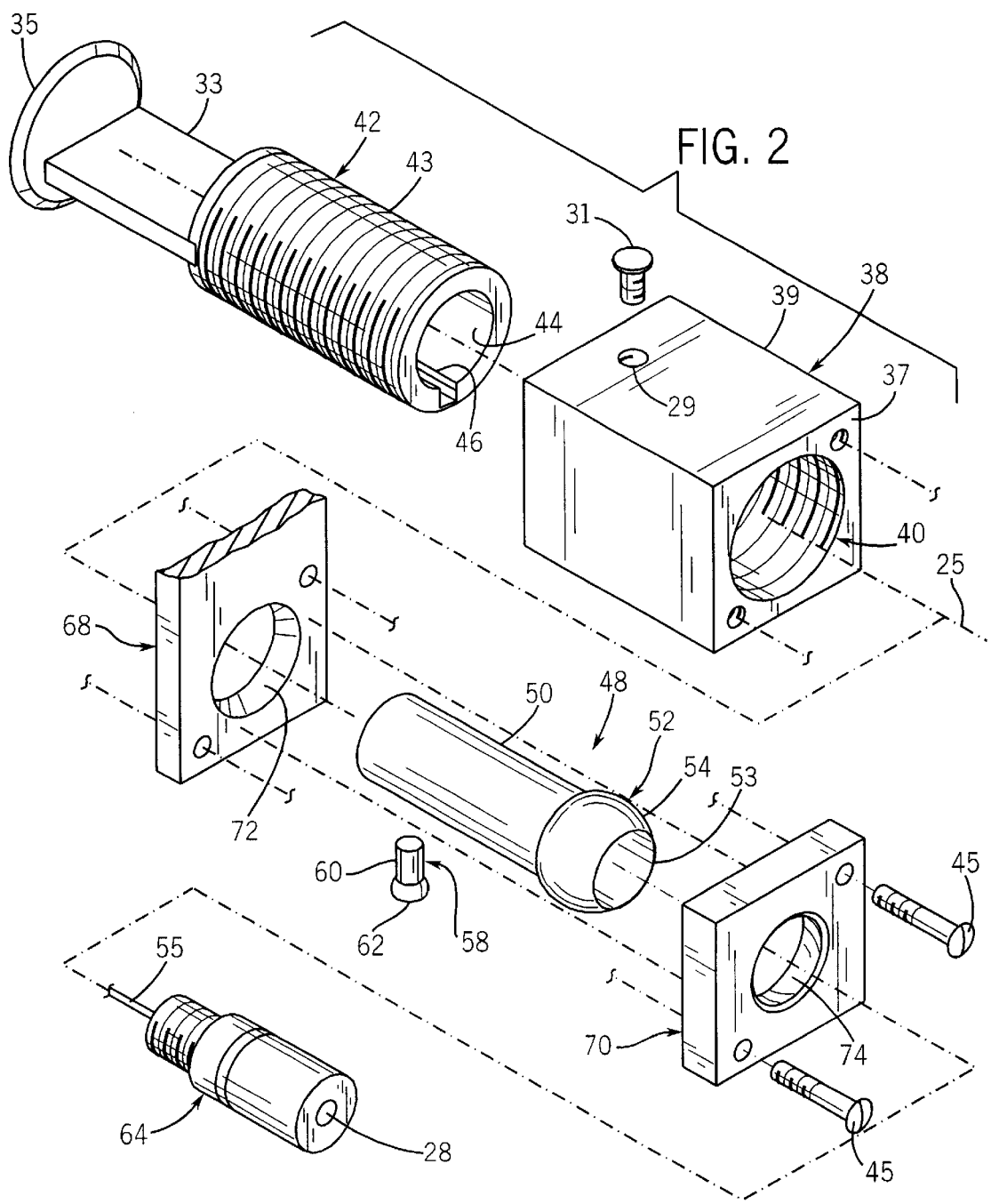
FIG. 2 is an exploded assembly view of the laser assembly illustrated in FIG. 1.
Figure 3:
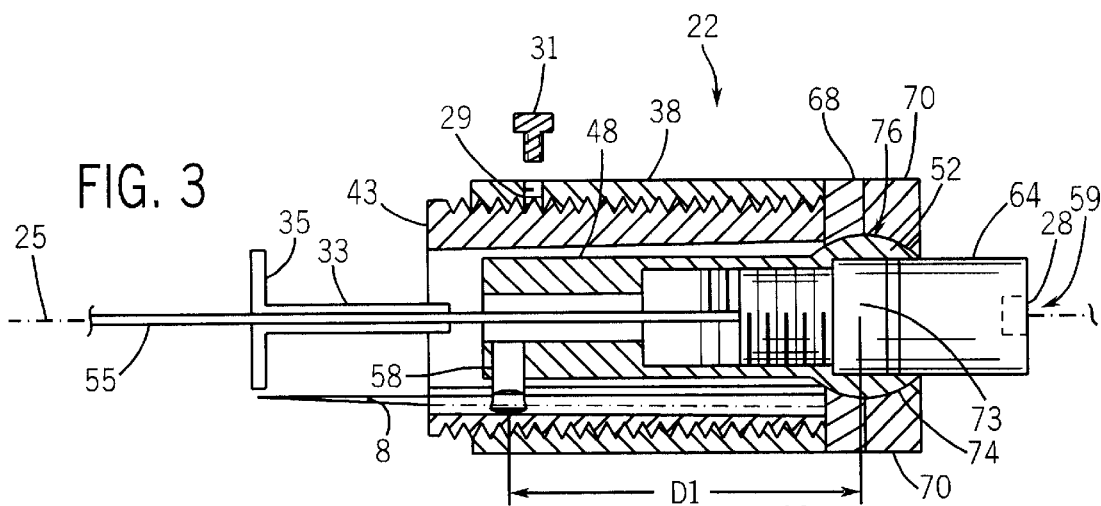
FIG. 3 is a sectional side elevation view of the laser assembly taken along lines 3—3 of FIG. 1 and shown in a contracted position.

Referring now to FIGS. 2 and 3, the components of the laser assembly 22 comprise a screw block 38 having an outer surface 39, and a threaded annular opening 40 extending axially therethrough. The outer surface 39 is rectangular in cross-section and mounted onto the outer surface 24 of the MRI system. The opening 40 is threaded and configured to accept therein a corresponding plurality of threads 43 of a screw 42. Accordingly, the screw 42 is translatable with respect to the screw block 38 by rotating the screw therein, about an axis of rotation 25, via a thumb wheel 35 that is connected to the outer end of the screw 42 via a shaft 33. The shaft 33 has a length sufficient such that the thumb wheel 35 extends beyond the outer housing of the MRI system so as to be accessible to a user. It should be appreciated, however, that the thumbwheel could be configured to receive the bit of a screwdriver and, in this configuration, the thumbwheel would not need to extend beyond the outer housing of the MRI system. The screw block 38 includes an opening 29 extending radially through the outer housing 39 that is configured to receive a set screw 31 to lock the position of the screw 42 with respect to the screw block 38 when the screw is in its desired position, as will be described in more detail below.

The screw 42 comprises an annulus, in accordance with the preferred embodiment, whose inner surface 44 includes a generally axially directed groove that forms a ramp 46. In particular, the ramp 46 comprises an elongated groove that is formed in the inner surface 44. The ramp 46 extends generally in the direction of the axis of rotation 25, and is sloped such that the end of the ramp adjacent a laser beam emitting end 59 is closer to the axis of rotation than the opposite end of the ramp. In accordance with the preferred embodiment, the ramp 46 has a slope of 1° with respect to the axis of rotation 25.

A laser module housing 48 is received in the opening of the screw 42. It comprises an elongated hollow annular body 50 having an outer diameter smaller than the inner diameter of the screw 42 and it further defines a ball 52 having a spherical outer surface 54 disposed at one end. An axially directed opening 53 extends through the housing 48 and defines a laser beam emitting end 29 at the ball 52.

A slide stud 58 is connected to the outer surface of the laser module housing 48 at the end opposite the ball 52 and extends radially outwardly therefrom. The slide stud 58 comprises a cylindrical body 60 having an outwardly disposed flange 62 whose outer diameter is greater than that of the cylindrical body 60. In cross-section, the ramp 46 has a throat of reduced width with respect to the groove to accommodate the flange 62 of slide stud 58. Accordingly, the flange 62 is locked in the ramp 46 with respect to radial movement, allowing the slide stud 58 to slide within the ramp when the screw 42 is rotated with respect to the screw block 38. In operation, rotation of screw 42 additionally rotates the slide stud 58, which in turn rotates the laser module housing 48 a laser module 64, which will now be described.

The laser module 64 is disposed within the laser module housing 48 and attached thereto. It includes the laser emitting diode 28 mounted at one end, and the laser beam 26 is emitted generally along the central axis 25 of the laser module housing 48 from its emitting end 59. An electrical wire 55 extends from the other end of the module 64 opposite the diode 28 and is connected to a power supply (not shown) that activates the diode. The wire may 55 be supported within the shaft 33, or may alternatively hang out the rear end of the laser assembly 22.

Figure 4:
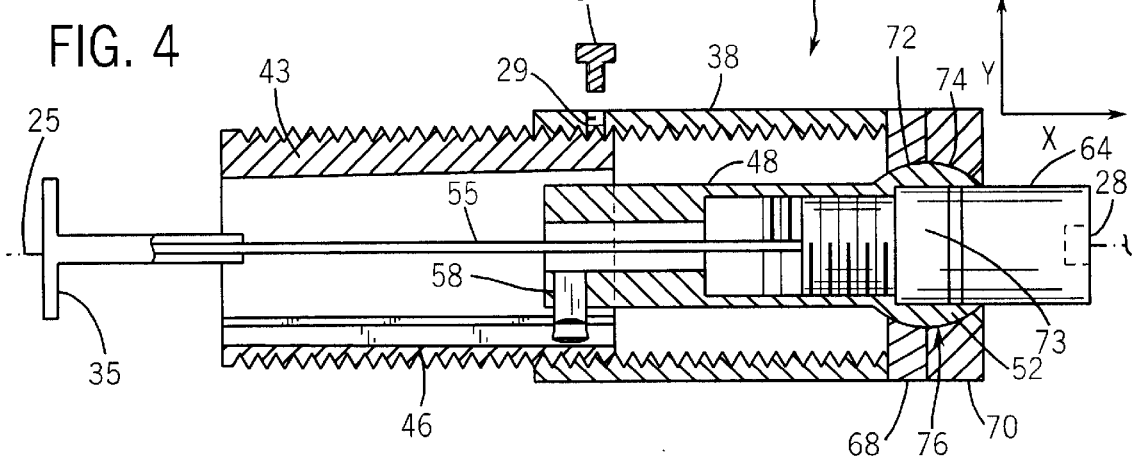
FIG. 4 is a sectional side elevation view of the laser assembly illustrated in FIG. 3 shown in an extended position.

Referring particularly to FIGS. 3 and 4, inner and outer ball socket retainer plates 68 and 70 are connected to each other and mounted to the front face 37 of the screw block 38 via screws 45 or the like. Each plate 68 and 70 has an axially aligned hollow interior which together form concave surfaces. The concave surfaces 72 and 74 for a spherical connection so as to entrap the ball 52 on the housing 48 to form a socket 76 that retains the housing 48 and permits the ball 52 to swivel therein. This ball and socket connection permits the housing 48 and enclosed laser module 64 to be moved to adjust the direction of the emitted laser beam 26.

Referring now also to FIG. 4, when the screw 42 is rotated counterclockwise, such as by rotating thumb wheel 35, the screw will move axially outwardly in the "z" direction with respect to the screw block 38. The assembly will move from its contracted position illustrated in FIG. 3 to its extended position illustrated in FIG. 4. As the screw 42 is rotated, the slide stud 58 will rotate therewith which, in turn will additionally rotate the laser module housing 48 and laser module 64. Alternatively, the laser module 64 could be rotatably fixed such that the housing 48 rotates with respect to the laser, causing the laser diode 28 to tilt, as will become apparent to one having ordinary skill in the art from the description below.

The slide stud 58, laser module housing 48, and laser module 64 will not translate in the axial direction along with the screw 42, however, as the ball 52 is axially fixed in the socket 76. Accordingly, the slide stud will slide along the ramp 46 as the screw 42 is translated with respect to the laser module housing 48. It should be appreciated that a lubricant may be applied to the ramp 46 to allow the slide stud 58 to more easily slide therealong.

Figure 5:
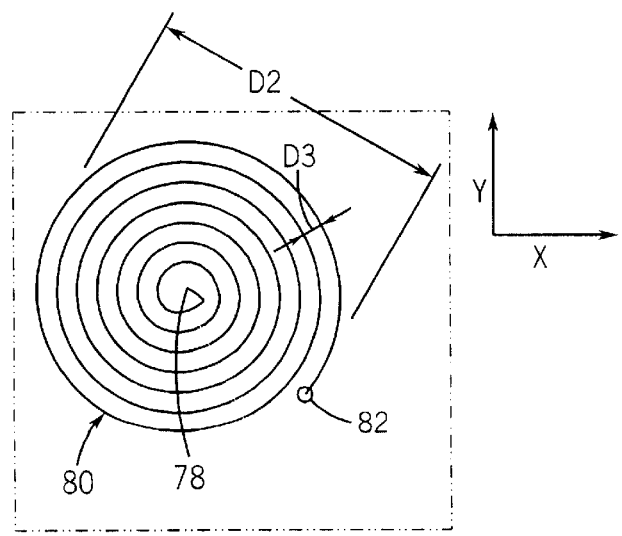
FIG. 5 is a schematic illustration of the path of the laser beam in accordance with the preferred embodiment.

Because the ramp 46 is sloped, the rear end of the laser module housing 48 will be moved radially outward from the central axis 25 as the screw is rotated to swivel, or wobble, the housing 48 in the ball and socket connection. The directed laser 26 will therefore be aimed increasingly away from the central axis 25. As the thumb wheel 35 is rotated to translate the screw 42 within screw block 38, the housing 48 is wobbled such that the laser beam 26 maps out a spiral path on any target in its path, as shown in FIG. 5. The amount of this wobble, and hence the radius of the resulting beam path 80, is at least partially dependent on the pivot radius of the laser module housing 48, which is the distance D1 between the center 73 of ball 72 and the center of slide stud 58, as will be described in more detail below.

In accordance with the preferred embodiment, the spiral path of the laser beam 26 is the result of the laser module 64 rotating along with the laser module housing 48. Alternatively, if the laser module 64 is fixed with respect to rotational movement, as described above, the laser diode 28 would be progressively tilted with the rotation of the housing 48.

In operation, when the laser assembly 22 is initially installed in an MRI system, or when the laser is to be periodically calibrated, the laser beam 26 will initially be pointed towards an origination location 78 that offset from the mirror 30 in both the "x" and "y" directions. However, because the laser beam 26 and mirror 30 are hidden from the user's vision, the user will not know how the orientation of the laser diode 28 is to be adjusted so as to translate the beam towards a destination location 82 disposed on the deflection surface 32 of mirror 30. Rather, the user will only be able to observe the calibration surface and infer that the beam 26 is properly aligned with the destination location 82 when the beam identifies a target on the calibration surface (not shown) that is positioned within the MRI system.

By rotating the screw 43, the user is able to utilize the resulting spiral path 80 of the laser beam 26 to locate the destination location 82. Assuming the radius of spiral 80 produces sufficient coverage for the laser beam 26, as indicated by the distance D2 in FIG. 5, the laser beam will eventually hit the destination location 82. It should be apparent that the number of revolutions the beam 26 makes as it spirals outward must be sufficient that the distance between adjacent radii in the spiral path 80 is less than the target size. This radial resolution is determined primarily by the slope of the ramp 46. When the target is hit, the beam 26 will deflect approximately 90° and extend radially inwardly through the opening 23 in the housing 24 and onto the calibration surface. The user will then cease rotating the screw 42, and will tighten the set screw 31 to prevent the screw 42, and laser beam 26, from slipping during use of the MRI system.

As can be seen in FIG. 5, the illustrated spiral 80 is sufficiently tight so as to prevent the beam 26 from passing over the destination location 82, and additionally has sufficient coverage to ensure that the target is within the range of the laser beam. Spiral tightness is defined as the distance D3 between individual passes of the laser beam 26. However, if the width of the destination location 82 with respect to the beam is less than the spiral tightness, the user will run the risk of the beam 26 passing over the target. Additionally, the destination location 82 may be missed if the spiral has insufficient coverage. For example, if the destination location 82 is disposed far from the origination point, and the spiral 80 that is produced after the screw 42 is fully extended is not sufficiently large, the beam 26 will not reach the target.

It should be appreciated in this regard that several characteristics of the laser assembly may be varied that will affect the properties of the spiral 80 in a predictable manner, thereby affecting the probability of the laser beam becoming successfully aligned with the destination location 82. For instance, referring to Table 1 below, the tightness of the and maximum coverage of the spiral 80 may be adjusted by varying the configuration of the laser assembly 22 which will, in turn vary the sensitivity of the laser assembly by varying the spiral coverage per unit length of screw movement as well as the maximum number of screw turns until the screw 32 is fully extended. It should be appreciated in Table 1 that the parameters of the laser assembly are assumed to be varied without changing the length of the screw 32.

Examples of characteristics of the laser assembly 22 that could be varied include the pitch of the threads (threads/inch) of screw 42, the slope of the ramp 46, and the pivot radius of the laser module housing 48.

In accordance with the preferred embodiment, the threads of screw 42 have a pitch diameter of ¾" and a corresponding pitch of 16 (threads/inch), the slope of ramp 46 is 1°, and the pivot radius is 29.4 mm, which yields a spiral coverage of 9.2 mm for every half-inch that the screw 42 is translated. If the thread pitch is increased, the spiral tightness will also increase while maintaining the coverage constant. If the slope is increased, the spiral tightness will decrease while increasing the spiral coverage. If the pivot radius is increased, the spiral tightness will increase while the available coverage is maintained constant.

Therefore, if increased spiral coverage is desired, the user could increase the slope of the ramp 46. However, doing so would also decrease the spiral tightness. Accordingly, depending on the size of the destination location 82, the thread pitch or pivot radius may be increased to yield a tighter spiral 80. It should be appreciated, however, that increasing the pivot radius would also decrease the coverage. Accordingly, it may be desirable to increase the thread pitch.

TABLE 1

| Spiral Property | Thread Pitch ↑ | Slope ↑ | Pivot Radius ↑ |
| --- | --- | --- | --- |
| Tightness | ↑ | ↓ | ↑ |
| Coverage | ↔ | ↑ | ↓ |
| Coverage per Unit Screw Shift | ↔ | ↑ | ↓ |
| Max No. Turns | ↑ | ↔ | ↔ |

↑ indicates an increase: ↓ indicates a decrease: ↔ indicates no change

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements included within the spirit and scope of the invention, as set forth by the appended claims.

What is claimed is:

1. An apparatus for systematically aiming a laser beam to a hidden target in an MRI machine, comprising:

an outer housing extending generally along a central axis;

a laser diode operable to emit the laser beam in a general direction of the hidden target;

an adjustable coupling for mounting the laser diode to the outer housing; and a manually operated actuator in mechanical communication with the coupling being operable to systematically move the laser beam in a spiral search path that intersects with the hidden target, wherein the spiral has a resolution between adjacent revolutions that is smaller than the target; and a laser module housing the laser diode and having a protrusion extending therefrom, wherein the apparatus further includes a ramp that engages the protrusion to move the laser beam in the spiral search path.

2. The apparatus as recited in claim 1, wherein the coupling further comprises a locking mechanism to lock the coupling in place when the laser beam is aligned with the target.

3. The apparatus as recited in claim 1, wherein the laser diode is mounted onto a magnetic resonance imaging device, and wherein the target comprises a reflective surface mounted onto the magnetic resonance imaging device.

4. An apparatus for systematically aiming a laser beam to a target in an MRI machine, comprising:

an outer housing extending generally along a central axis;

a laser diode operable to emit the laser beam in a general direction of the target;

an adjustable coupling including an elongated inner housing that is threadedly connected to the outer housing for mounting the laser diode to the outer housing, wherein the coupling is rotatable about an axis of rotation and translatable along a sloped ramp to systematically move the laser beam in a spiral search path that intersects with the target; and a laser module housing the laser diode and having a protrusion extending therefrom, wherein the ramp is disposed in the inner housing that is sloped with respect to the axis of rotation and configured to accept the protrusion therein.

5. The apparatus as recited in claim 4, wherein the laser module is axially fixed with respect to the outer housing and rotatable along with the inner housing, wherein the protrusion slides along the ramp to displace the laser diode during rotation.

6. The apparatus as recited in claim 5, wherein the outer housing further comprises a socket that supports at least a portion of the laser module.

7. The apparatus as recited in claim 4, wherein the inner housing further comprises an actuator extending outwardly therefrom that is rotatable to correspondingly rotate the inner housing.

8. The apparatus as recited in claim 4, wherein the coupling further comprises a locking mechanism to lock the position of the coupling when the laser beam is aligned with the target.

9. The apparatus as recited in claim 7, wherein the actuator is manually activated.

* * * * *